United States Patent
D'Angelico et al.

(10) Patent No.: US 6,389,891 B1
(45) Date of Patent: May 21, 2002

(54) METHOD AND APPARATUS FOR ESTABLISHING AND/OR MONITORING THE FILLING LEVEL OF A MEDIUM IN A CONTAINER

(75) Inventors: Sascha D'Angelico; Sergej Lopatin, both of Lörrach (DE)

(73) Assignee: Endress + Hauser GmbH + Co., Maulburg (DE)

( * ) Notice: Subject to any disclaimer, the term of this patent is extended or adjusted under 35 U.S.C. 154(b) by 0 days.

(21) Appl. No.: 09/577,100

(22) Filed: May 24, 2000

(30) Foreign Application Priority Data

Mar. 24, 2000 (DE) .......................... 100 14 724

(51) Int. Cl.⁷ .......................... G01F 23/00; G01N 9/00
(52) U.S. Cl. .................... 73/290 V; 73/32 R; 73/304 R
(58) Field of Search .................... 73/290 R, 290 V, 73/32 R, 304 R, 649, 651; 340/612, 620

(56) References Cited

U.S. PATENT DOCUMENTS

| | | | |
|---|---|---|---|
| 4,594,584 A | * 6/1986 | Pfeiffer et al. | 340/620 |
| 4,740,726 A | 4/1988 | Umezawa | |
| 4,922,745 A | 5/1990 | Rudkind et al. | |
| 5,191,316 A | * 3/1993 | Dreyer | 340/621 |
| 5,625,343 A | * 4/1997 | Rottmar | 340/620 |
| 5,815,079 A | * 9/1998 | Getman et al. | 340/620 |
| 6,148,665 A | * 11/2000 | Getman et al. | 73/290 V |
| 6,236,322 B1 | * 5/2001 | Lopatin et al. | 340/612 |

FOREIGN PATENT DOCUMENTS

EP          0 282 251        3/1988

* cited by examiner

Primary Examiner—Hezron Williams
Assistant Examiner—Katina Wilson
(74) Attorney, Agent, or Firm—Bose McKinney & Evans LLP

(57) ABSTRACT

The invention relates to a method and an apparatus for establishing and/or monitoring the filling level of a medium in a container and to the determination of the density of a medium in a container.

It is the object of the invention to propose a method and an apparatus which permit reliable determination and/or monitoring of the filling level or the density of a medium.

With reference to the apparatus according to the invention, the object is achieved by virtue of the fact that at least a first mode and a second mode of the oscillations of the oscillable unit (2) are evaluated, and the evaluated modes are used to detect a change in mass at the oscillable unit (2).

38 Claims, 5 Drawing Sheets

METHOD AND APPARATUS FOR ESTABLISHING AND/OR MONITORING THE FILLING LEVEL OF A MEDIUM IN A CONTAINER

The invention relates to a method and an apparatus for establishing and/or monitoring the filling level of a medium in a container and to the determination of the density of a medium in a container in accordance with the preamble of claims 1 and 10, respectively.

Apparatuses having at least one oscillating element, so-called vibration detectors, for detecting or for monitoring the filling level of a medium in a container have already become known. The oscillating element is usually at least one oscillating bar which is fastened to a diaphragm. The diaphragm is excited to oscillate via an electromechanical transducer, for example a piezoelectric element. The oscillations of the diaphragm also cause the oscillating element fastened to the diaphragm to execute oscillations.

Vibration detectors constructed as filling level measuring instruments utilize the effect that the oscillation frequency and the oscillation amplitude depend on the respective degree of coverage of the oscillating element: whereas the oscillating element can execute its oscillations freely and undamped in air, it experiences a change in frequency and amplitude as soon as it is immersed partially or completely in the medium. Consequently, a predetermined change in frequency (the frequency is usually measured) can be used to draw an unambiguous conclusion on the achievement of the predetermined filling level of the medium in the container. Furthermore, filling level measuring instruments are chiefly used as protection against overfilling or for the purpose of safeguarding against pumps running dry.

Moreover, the damping of the oscillation of the oscillating element is also influenced by the respective density of the medium. Consequently, in the case of a constant degree of coverage there is a functional relationship with the density of the medium, with the result that vibration detectors are better suited both for determining filling level and for determining density. In practice, for the purpose of monitoring and detecting the filling level or the density of the medium in the container the oscillations of the diaphragm are picked up and converted into electrical reception signals with the aid of at least one piezoelectric element.

The electrical reception signals are subsequently evaluated by an electronic evaluation system. In the case of determining the filling level, the electronic evaluation system monitors the frequency of oscillation and/or the amplitude of oscillation of the oscillating element and signals the state of "sensor covered" or "sensor uncovered" as soon as the measured values undershoot or overshoot a prescribed reference value. An appropriate message to the operating staff can be made optically and/or acoustically. A switching operation is triggered as an alternative or in addition; for example, a feed valve or discharge valve on the container is opened or closed.

The instruments previously mentioned for measuring the filling level or the density are used in many sectors of industry, for example in the chemical industry, in the foodstuffs industry or in water treatment. The bandwidth of the monitored charge materials ranges from water through yoghurt, colorants and coatings to highly viscous charge materials such as honey or up to greatly foaming charge materials such as beer.

The measurement of filling level or density by means of vibration detectors encounters problems due to the fact that there is no unique relationship between a change in frequency which occurs and the degree of coverage or the density of the medium. An important influencing quantity which makes itself felt just like the coupling to the mass of the medium in a shift in the resonant frequency is the change in mass of the oscillable unit. A change in mass can be caused both by the formation of coating, that is to say by the formation of deposits of the medium on the oscillable unit, and by the corrosion of the oscillating bars. Depending on the type of change in mass and its degree, it is possible here for the most highly undesired case to occur, that the sensor is permanently "covered" or "uncovered", and thus that it is reported that the predetermined filling level has been reached although the limit filling level has not yet been reached. A similar statement holds with regard to the measurement of density: the false density of the medium is measured and indicated.

It is the object of the invention to propose a method and an apparatus which permit reliable determination and/or monitoring of the filling level or the density of a medium.

The object is achieved with regard to the method by virtue of the fact that at least a first mode and a second mode of the oscillations of the oscillable unit are evaluated, and that the evaluated modes are used to detect a change in mass of the oscillable unit. Although exclusive reference is frequently made below to an increment in mass which occurs in the event of the formation of coating on the oscillable unit, comparable considerations hold, of course, for the loss of mass which can be, inter alia, a consequence of the corrosion of the oscillating bars.

The invention is based on the physical effect that different oscillation modes are formed upon excitation of the oscillable unit. It is set forth below in yet more detail which different oscillation modes occur for a vibration detector having, for example, paddle-shaped oscillating bars.

In accordance with an advantageous development of the method according to the invention, it is provided that modes whose oscillations are differently influenced by the medium are evaluated as first and second mode.

A preferred variant of the method according to the invention proposes that the first mode is a mode whose oscillations are essentially independent of the medium, and that the second mode is a mode whose oscillations are influenced by the medium. In concrete terms, this means that the first mode is selected as a mode whose natural frequency or resonant frequency is shifted as a consequence of a change in mass, but whose resonant frequency remains essentially unchanged when the oscillable unit comes into contact with the medium. Consequently, the first mode can be any mode in which the cross-sectional surfaces of the "oscillating bars/medium" of the oscillating bars are small in the direction of oscillation. If this precondition is fulfilled, the interaction of the oscillable unit with the medium, and thus the mass coupling of the oscillable unit to the medium is relatively weak. Selected as second mode is a mode whose natural frequency changes strikingly as soon as the oscillable unit comes into contact with the medium.

An advantageous development of the method according to the invention provides that a change in the first mode whose oscillations are essentially independent of the medium is used to detect whether a change in mass has occurred at the oscillable unit. It is provided, in particular, that a change in frequency of the oscillations of the first mode is used to detect a formation of coating or a loss in mass at the oscillable unit.

Whereas the previously described first variant of the method according to the invention provides for the selection of two modes which exhibit entirely different reactions as a consequence of the change in mass or as a consequence of the contact with the medium, a second variant adopts a different avenue. In accordance with the alternative second variant of the method according to the invention, it is provided to select two modes as first mode and as second mode of the oscillations of the oscillable unit, the two modes respectively having a first component which is a function of the coupling to the mass of the medium, and the two modes having a second component which is independent of the coupling to the mass of the medium and which depends only on the respective mass of the oscillable unit.

An advantageous development of the method according to the invention provides for drawing conclusions on the change in mass of the oscillable unit with the aid of the functional relationship of the first and the second modes of the oscillations of the oscillable unit on the medium and on the mass of the oscillable unit. The sole requirement which is to be made of the selection of the two modes is that they differ sufficiently from one another.

The determination of the influence of the formation of coating on the measured values is preferably performed via a system of equations which is composed of the two formulas named below:

$$\Delta F_C = f_C^1(m_k) + f_C^2(m_a)$$
$$\Delta F_D = f_D^1(m_k) + f_D^2(m_a)$$

The symbols used in this system of equations characterize the following variables:

$\Delta F_c$: the relative frequency shift of a first mode;
$\Delta F_D$: the relative frequency shift of a second mode;

$$\Delta F[\%] = \left(\frac{F_{measure}[\text{Hz}]}{F_{air, without\_coating}[\text{Hz}]} - 1\right) * 100\%$$

the term respectively symbolizing the relative frequency shift in the natural frequency of the corresponding mode, relative meaning that the measured frequency shift is expressed in percent with reference to the corresponding natural frequency in air without the formation of coating.

$m_k$: a measure of each type of mass coupling to and damping by the medium. Here—as already described earlier—in addition to the depth of immersion h of the oscillable unit, a role is also played by the density $\rho$ of the medium and the viscosity $\eta$ of the medium. In computational terms this can be expressed by the following functional relationship: $m_k = f(h; \rho, \eta)$;

$m_a$: the coating mass;

$f_c^1(m_k)$, $f_D^2(m_k)$: the frequency shift curves of two sufficiently different modes (for example, mode C and mode D) of the oscillable unit, as a function of the mass coupling $m_k$ of the oscillable unit, and the damping of the oscillable unit by the medium (→ immersion curves);

$f_c^2(m_a)$, $f_D^2(m_a)$: the frequency shift curves of two sufficiently different modes (for example, mode C and mode D) of the oscillable unit as a function of the formation of coating $m_a$ on the oscillable unit (→ coating curves).

An advantageous refinement of the method according to the invention provides that an error message is output when the changes in frequency, caused by change in mass of the oscillable unit, of a first and/or a second mode of the oscillations of the oscillable unit overshoot a prescribed desired value.

It is particularly advantageous when a change, caused by change in mass at the oscillable unit, in a first and/or a second mode of the oscillations of the oscillable unit is used for the purpose of undertaking inline correction of the measured data of the oscillable unit.

With reference to the apparatus according to the invention, the object is achieved by virtue of the fact that the control/evaluation unit uses at least a first mode and a second mode of the oscillations of the oscillable unit for the purpose of evaluation, and that the control/evaluation unit detects a change in mass at the oscillable unit with the aid of the evaluated modes.

An advantageous refinement of the apparatus according to the invention provides that the evaluation/control unit is integrated into the apparatus for determining and/or monitoring the filling level and/or for determining the density of the medium. The apparatus according to the invention is in this case a so-called compact sensor. The error message can be digitally output, for example optically, acoustically and/or via at least two data lines.

A refinement of the apparatus according to the invention which is alternative to the compact sensor provides at least two data lines via which the measured data are led to the evaluation/control unit or via which the evaluation/control unit communicates with a remote control point. It is particularly advantageous in this connection when the respective measured data and/or correction data are transmitted digitally to the remote control point. By contrast with analog data transmission, digital data communication has the known advantage of increased interference immunity. Of course, recourse may be made to the known transmission protocols and transmission standards for the communication.

In accordance with a preferred development of the apparatus according to the invention, an output unit is proposed which outputs an error message to the operating staff optically and/or acoustically when, preferably within the limits of prescribed tolerance values, a prescribed desired value of the change in frequency which is to be ascribed to a change in mass of the oscillable unit is overshot or undershot.

Moreover, it is advantageously provided that the control/evaluation unit is assigned a storage unit in which desired values are stored for tolerable changes in frequency which originate from a change in mass.

The invention is explained in more detail with the aid of the following drawings, in which.

Figure 2A:
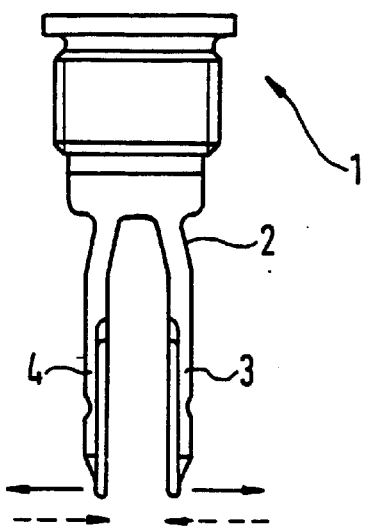
FIG. 2 shows possible, selected oscillation modes of a preferred oscillable unit with two paddle-shaped oscillating bars.
Figure 2B:
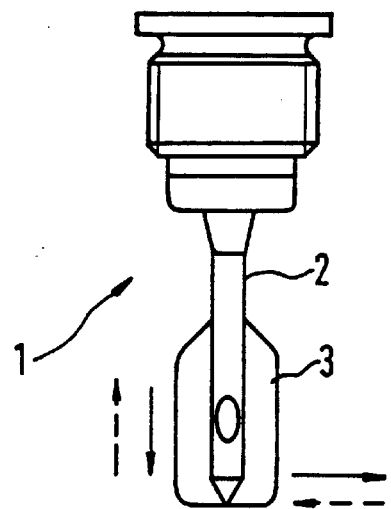
Figure 2C:
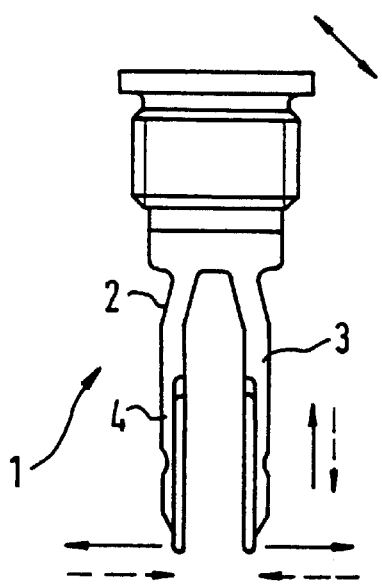
Figure 2D:
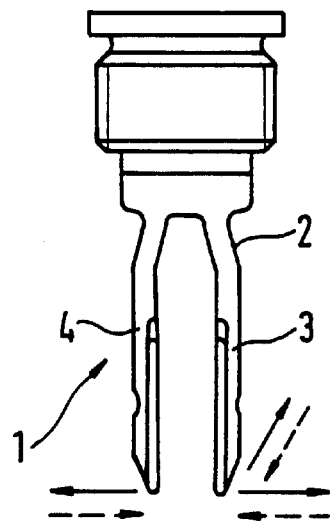
Figure 3:
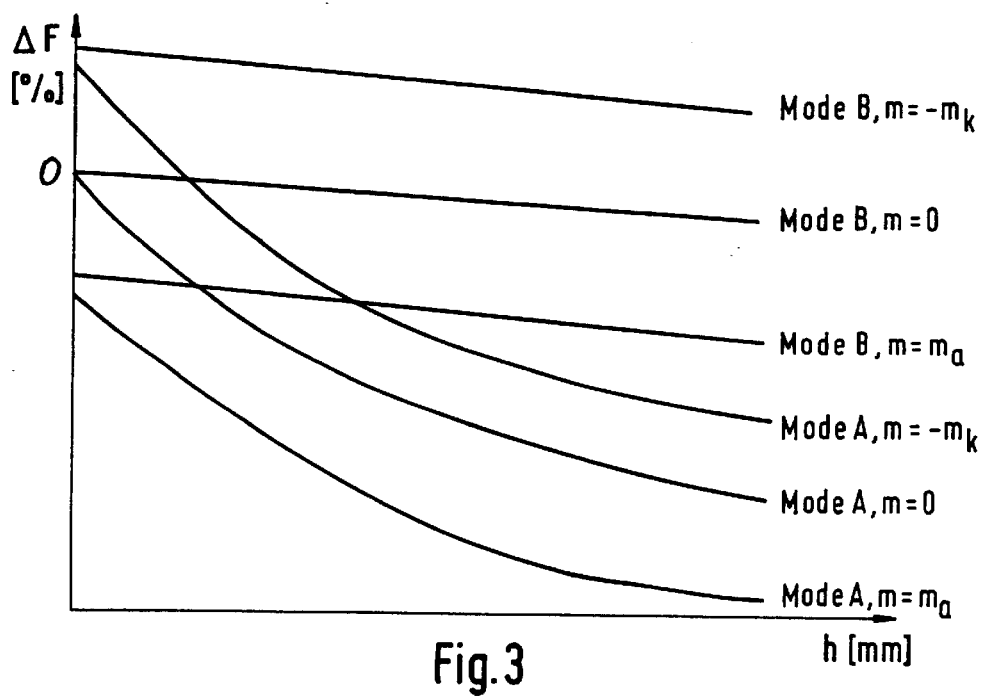
Figure 4:
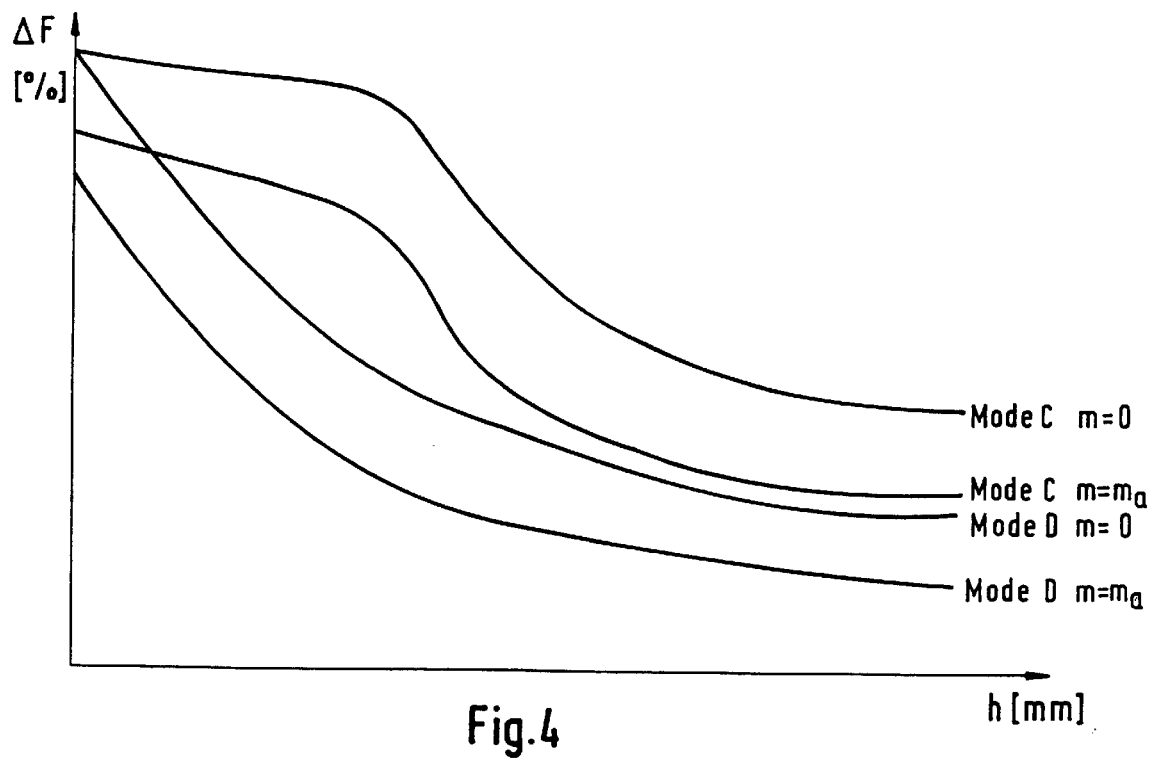
Figure 5:
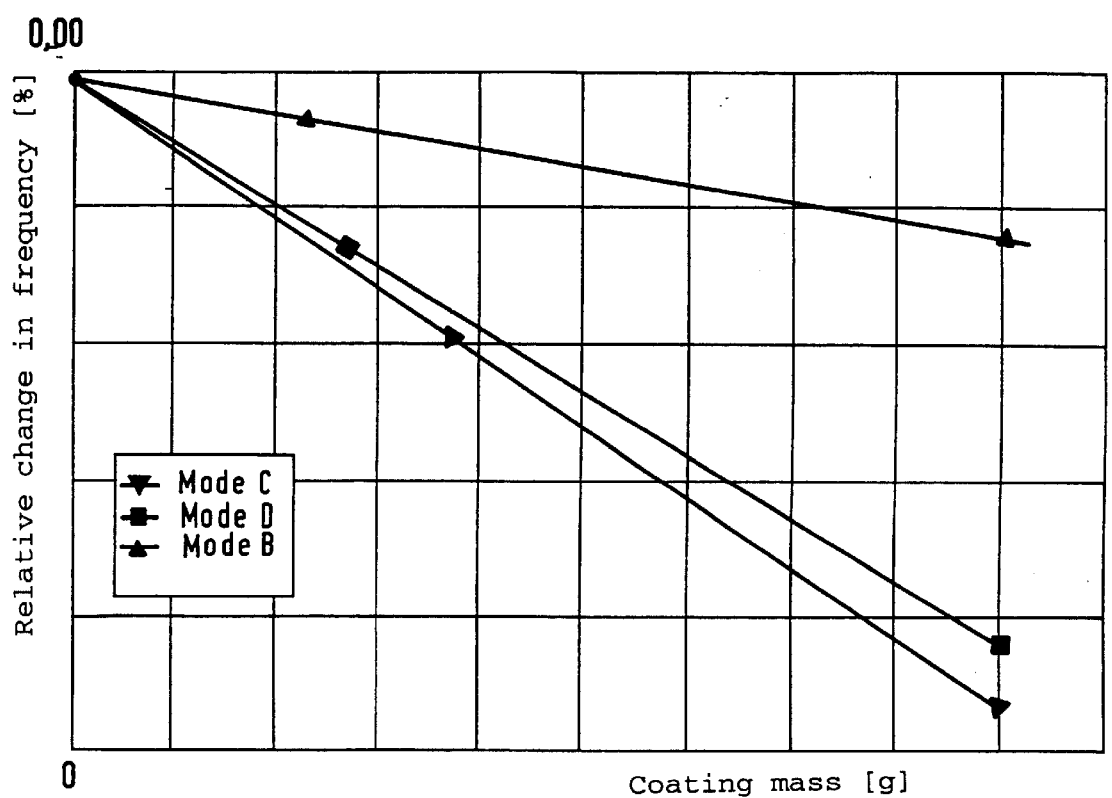
Figure 6:
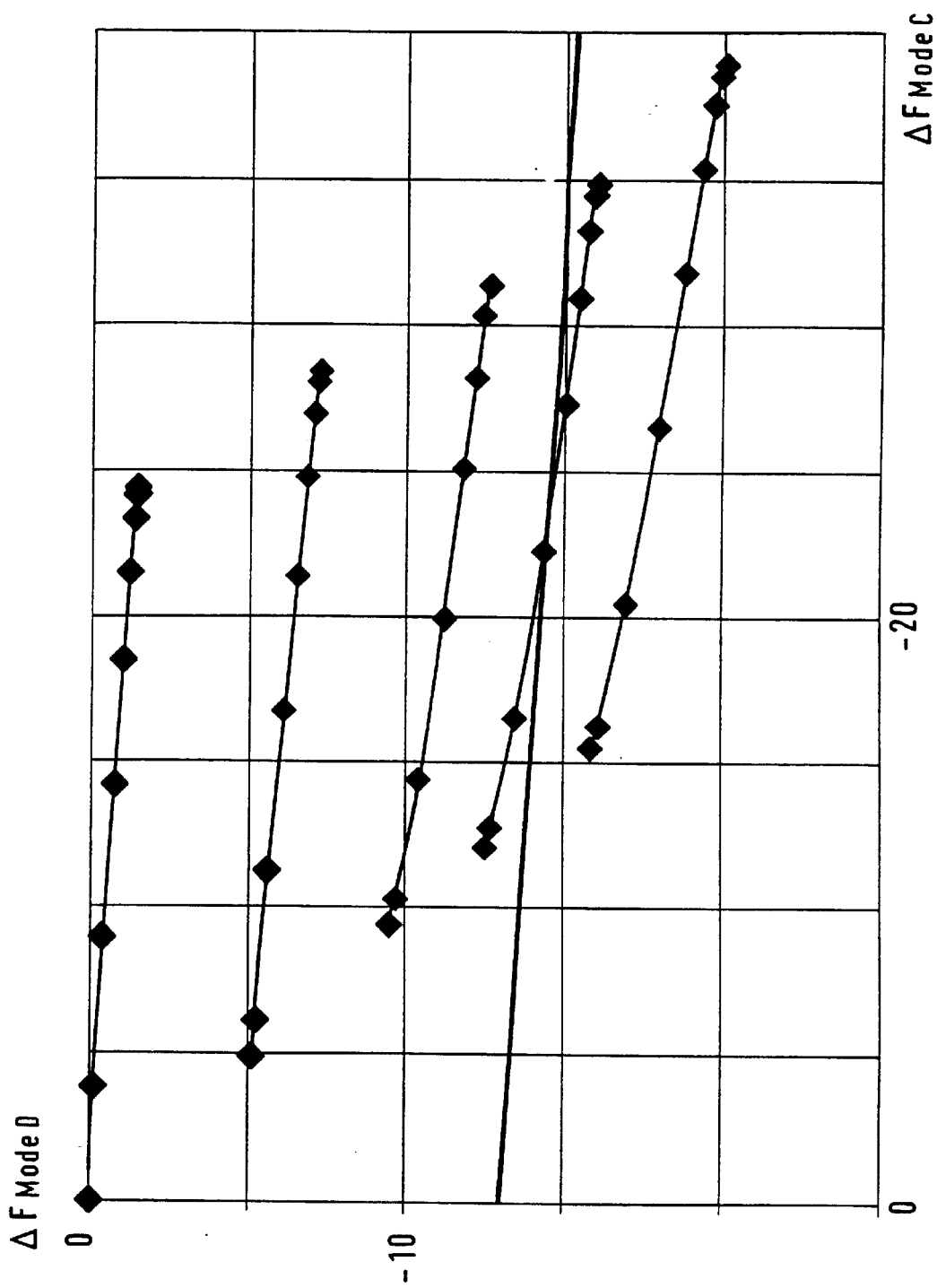

a) mode A, in which a change in frequency which occurs is influenced by the mass coupling to the medium, b) mode B, in which a change in frequency which occurs essentially originates from the formation of coating, c) mode C, in which the change in frequency is influenced both by the formation of coating and by the coupling to the mass of the medium, and d) mode D, in which the change in frequency is influenced both by the formation of coating and by the coupling to the mass of the medium, FIG. 3 shows sketches of immersion curves of the modes A and B, illustrated in FIGS. 2a and 2b, with and without coating mass and in the case of a negative change in mass, FIG. 4 shows sketches of immersion curves of the modes illustrated in FIGS. 2c and 2d, with and without coating mass, FIG. 5 shows a schematic of the coating curves of different modes in air, and FIG. 6 shows a graph of the tuples of the change in frequency.

Figure 1:
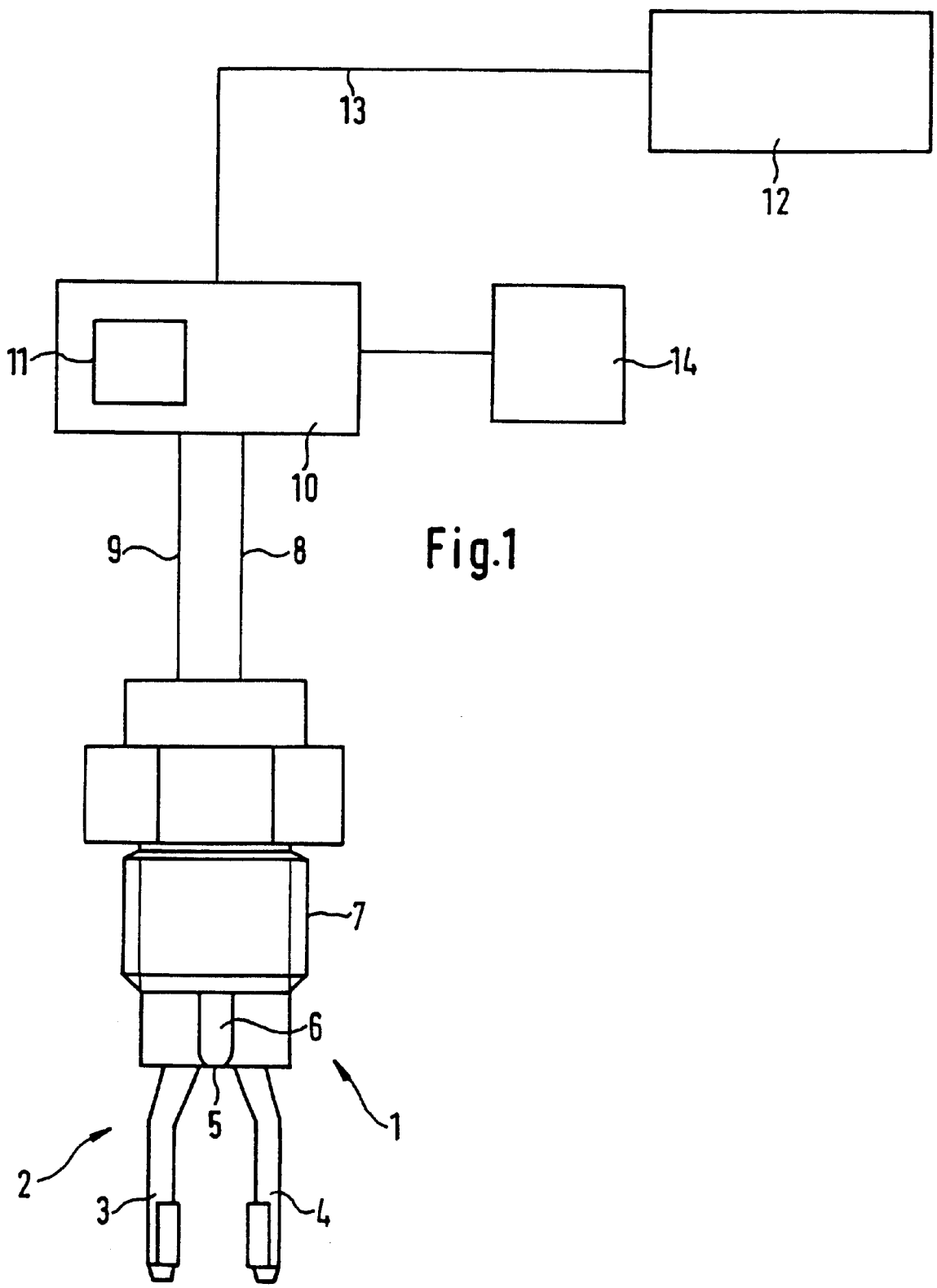
FIG. 1 shows a schematic of the apparatus according to the invention.

FIG. 1 shows a schematic of the apparatus 1 according to the invention for establishing and/or monitoring the filling level of a medium in a container—it may be said that the container and medium are not separately illustrated in FIG. 1. As already explained previously, the apparatus 1 shown in FIG. 1 is suitable both for detecting filling level and for determining the density of the medium located in the container. Whereas in the case of the detection of filling level the oscillable unit 2 is immersed or not immersed in the medium only when the detected limit filling level is reached, for the purpose of monitoring or for the purpose of determining the density $\rho$ it must be immersed continuously into the medium up to a predetermined depth of immersion h. The container can be, for example, a tank or else a tube which is flowed through by the medium.

The apparatus 1 has an essentially cylindrical housing. Provided on the lateral surface of the housing is a thread 7. The thread 7 serves to fasten the apparatus 1 to the height of a predetermined filling level, and is arranged in a corresponding opening in the container. It goes without saying that other types of fastening, for example by means of a flange, can replace the screwing.

The housing of the vibration detector 1 is closed of by the diaphragm 5 at its end region projecting into the container (not shown), the diaphragm 5 being clamped in its edge region into the housing. The oscillable unit 2 projecting into the container is fastened to the diaphragm 5. In the case illustrated, the oscillable unit 2 is configured as a tuning fork, and therefore comprises two mutually spaced oscillating bars 3, 4 which are fastened to the diaphragm 5 and project into the container.

The diaphragm 5 is set oscillating by a drive/receiving element 6, the drive element exciting the diaphragm 5 to oscillate at a prescribed oscillating frequency. The drive element is, for example, a stack drive or a biomorph drive. Both types of piezoelectric drives are sufficiently known from the prior art and so a corresponding description can be dispensed with here.

Because of the oscillations of the diaphragm 5, the oscillable unit 2 also executes oscillations, the oscillation frequencies being different when the oscillable unit 2 is in contact with the medium and a coupling exists to the mass of the medium, or when the oscillable unit 2 can oscillate freely and without contact with the medium.

Just as in the case of the drive unit, the receiving unit can be a single piezoelectric element. The drive/receiving unit 6 excites the diaphragm 5 to oscillate as a function of a transmitted signal present at the piezoelectric element; furthermore, it serves to receive and convert the oscillations of the diaphragm 5 into electrical reception signals.

Because of this oscillating response of the piezoelectric element, the voltage difference causes the diaphragm 5 clamped into the housing to sag. The oscillating bars 3, 4, arranged on the diaphragm 5, of the oscillable unit 2 execute oppositely directed oscillations about their longitudinal axis because of the oscillations of the diaphragm 5. Modes with oppositely directed oscillations have the advantage that the alternating forces exerted by each oscillating bar 3, 4 on the diaphragm 5 cancel one another. This minimizes the mechanical stress of the clamping, with the result that approximately no oscillation energy is transferred to the housing or to the fastening of the vibration detector. Consequently, the fastening means of the vibration detector 1 are effectively prevented from being stimulated to execute resonant oscillations which could, in turn, interfere with the oscillations of the oscillable unit and falsify the measured data.

The electrical reception signals are relayed via data lines 8, 9 to the control/evaluation unit 10. The control/evaluation unit 10 is assigned a storage unit 11 in which there are stored desired values which permit the control/evaluation unit to detect a formation of coating on the oscillable unit 2 and, if appropriate, to exercise a correcting influence on the measured values. An error message is transmitted to the operating staff in the case shown via the output unit 14. Also to be seen in FIG. 1 is the control center 12 arranged apart from the vibration detector 1. The control/evaluation unit 10 and the control center 12 communicate with one another via the data line 13. It is preferred for the communication to be performed on a digital basis because of the enhanced interference immunity of the transmission.

FIGS. 2a, 2b, 2c and 2d show four selected and possible oscillation modes of an oscillable unit 2 with two oscillating bars 3, 4 constructed in the shape of paddles. In the case of the mode B illustrated in FIG. 2b, the immersion curve $\Delta F$ is essentially independent of the mass coupling $m_k$ to the medium, since the cross-sectional surfaces interacting with the medium are relatively small because of the oscillating movements which occur parallel to the paddle surface. The oscillation frequency is therefore essentially independent of the immersion depth h of the oscillable unit 2 into the medium, but it does exhibit a clear dependence on the coating mass $m_a$ present on the oscillating bars 3, 4. As already mentioned several times, similar considerations also hold for a loss of mass which occurs on the oscillable unit. Consequently, it is possible within the framework of certain tolerances to draw an unambiguous conclusion from a change in frequency $\Delta F$ of the mode B on the coating mass $m_a$ present on the oscillating bars 3, 4.

This functional relationship is to be seen as a graph in FIG. 3. FIG. 3 shows the immersion curves $\Delta F(h)$ of the modes A and B, illustrated in FIG. 2b, with and without coating mass $m_a$. Also illustrated in FIG. 3 are the corresponding immersion curves $\Delta F(h)$ for a negative change in mass of the oscillable unit 2, that is to say a mass loss $(m_k)$ on the oscillable unit 2; a mass loss occurs, for example, as a consequence of corrosion or mechanical wear of the oscillating bars 3, 4. The immersion curves $\Delta F(h)$, that is to say the change in frequency $\Delta F$ of the mode B as a function of the immersion depth h, approximately have the gradient of zero independently of the mass of the oscillable unit 2. Thus, they run essentially parallel to the x-axis. Logically, the change in frequency $\Delta F$ increases with rising or falling change in mass $m_a$. The immersion curves $\Delta F(h)$ of the mode A, likewise illustrated in FIG. 3, exhibit an entirely different behavior: here, a change in frequency is very clearly dominated by the immersion depth h of the oscillable unit 2 into the medium. Again, a positive or negative change in mass $m_a$, $m_k$ of the oscillable unit 2 is expressed in a parallel displacement of the immersion curves $\Delta F(h)$.

Both modes, mode A and mode B, are therefore best suited for use in connection with a first configuration of the method according to the invention. In accordance with the first variant of the method according to the invention, the determination of the degree of formation of coating (or the mass loss) is performed, specifically, with the aid of two modes, the first mode being a mode whose oscillations are essentially independent of the medium, and the second mode being a mode whose oscillations are essentially influenced only by the medium.

As proposed by an advantageous configuration of the method according to the invention, the change in frequency ΔF determined with the aid of the mode B dependent on the coating mass $m_a$ (or the mass loss) is used for inline correction of the measured data of the vibration detector 1. Furthermore, the information on the degree of formation of coating on the oscillable unit 2 or of the mass loss of the oscillable unit 2 can also be used for predictive maintenance purposes: the operating staff are shown or informed when the oscillable unit 2 must be cleaned or replaced by a unit 2 free from coating.

FIGS. 2c and 2d show two possible modes of an oscillable unit 2 with two oscillating bars 3, 4 which are constructed in the form of paddles and are preferably used in the second variant of the method according to the invention. It is assumed here that both modes C and D are dependent both on the mass coupling $m_k$ of the oscillable unit to the medium and on the coating mass which has formed on the oscillable unit. Furthermore, the two selected modes must differ from one another clearly with regard to their immersion curves ΔF(h). The fact that this is the case can be clearly seen with the aid of the sketched curves shown in FIG. 4.

Moreover, the coating curves $\Delta F(m_a)$ of modes A, B and C are illustrated in FIG. 5. Whereas mode B exhibits only a slight dependence on the coating mass $m_a$, modes C and D exhibit a strong dependence on a change in mass on the oscillable unit 2.

In formal mathematical terms, the immersion curves ΔF(h) of the two modes C and D can be described to a first approximation (the mixed term being neglected) by the following system of equations:

$$\Delta F_C = f_C^1(m_k) + f_C^2(m_a) \quad (1)$$

$$\Delta F_D = f_D^1(m_k) + f_D^2(m_a) \quad (2)$$

This system of equations must be solved in accordance with $m_a = f(\Delta F_0, \Delta F_x)$.

It follows from equation (1) that:

$$f_C^2(m_a) = \Delta F_C - f_C^1(m_k) \quad (3)$$

It follows from equation (2) that:

$$f_D^1(m_k) = \Delta F_D - f_D^2(m_a) \quad (4)$$

$$m_k = f_D^{-1}(\Delta F_D - f_D^2(m_a)) \quad (5)$$

Furthermore, it is preferred to apply a numerical method of solution.

It follows from (3) and (5) that:

$$f_C^2(m_a) = \Delta F_C - f_C^1\left[f_D^{-1}\left(\Delta F_D - f_D^2\left(f_C^{-2}(\Delta F_C - f_C^1(m_k))\right)\right)\right] \quad (6)$$

Furthermore, there is no need to specify an explicit formula for $m_a$, since finally interest attaches only to the relative change in frequency of mode C which is caused by the formation of coating. The limiting value for $f_c^{2\,(m_a)}$ must be fixed so as always to ensure a reliable detection of the predetermined filling level or the density of the medium within the tolerable limits.

The immersion curves and coating curves illustrated in FIG. 4 and FIG. 5 and preferably determined empirically can be approximated in a known way by means of approximation functions and thereby described mathematically.

The system of equations and the curves obtained by approximation can be used to determine for each measured tuple of frequency difference $\Delta F_C$, $\Delta F_D$ the value for $f_c^2(m_a)$, that is to say the relative change in frequency of mode C as a function of the coating mass $m_a$.

The measured values are plotted in FIG. 6 for the tuples of frequency difference against $\Delta F_C$, $\Delta F_D$. The measured points differ from one another with regard to the immersion depth h and/or with regard to the coating mass $m_a$ formed on the oscillable unit. The measured points with the same coating mass $m_a$ are connected to one another in each case in FIG. 7.

The measured values in the upper region of FIG. 6 represent the state of "low coating mass" while the measured values in the lower region represent the state of "high coating mass". In order to evaluate the measured data, it is therefore sufficient for the control/evaluation unit 10 to measure the changes in frequency of two sufficiently different oscillation modes, mode C and mode D in the case illustrated, and compare them with values which are stored in a table. The position of the measured values can then be used to make a clear distinction as to whether the formation of coating or the mass loss is still in the uncritical region, or whether an alarm must be triggered.

What is claimed is:

1. A method for determining at least one of a filling level and a density of a medium in a container, the method comprising the steps of:

exciting an oscillable unit to oscillate by means of an exciter oscillation;

detecting that a predetermined filling level has been reached as soon as the oscillable unit oscillates at an oscillation frequency which exhibits a predetermined frequency change with respect to a frequency of the exciter oscillation;

determining the density of the medium with the aid of the oscillation frequency of the oscillable unit; and evaluating at least a first mode and a second mode of the oscillations of the oscillable unit which exist while the oscillable unit is in contact with the medium to detect a change in mass at the oscillable unit.

2. The method as claimed in claim 1, wherein the evaluating step includes evaluating, as the first and second modes, modes whose oscillations are differently influenced by the medium.

3. The method as claimed in claim 2, wherein the first mode is a mode whose oscillations are essentially independent of the medium, and the second mode is a mode whose oscillations are essentially influenced by the medium.

4. The method as claimed in claim 2, wherein two modes are selected as first mode and as second mode of the oscillations of the oscillable unit (2), the two modes respectively having a first component which is a function of the medium, and the two modes having a second component which is essentially independent of the medium and depends essentially only on the respective mass of the oscillable unit (2).

5. The method as claimed in claim 2, further comprising the step of outputting an error message when changes in at least one of the first mode and the second mode of the oscillations of the oscillable unit, which changes are caused by the change in mass at the oscillable unit, overshoot a prescribed desired value.

6. The method as claimed in claim 2, further comprising the step of undertaking inline correction of the oscillation frequency of the oscillable unit based at least in part on a change, caused by a change in mass at the oscillable unit, in at least one of the first mode and the second mode of the oscillations of the oscillable unit.

7. The method as claimed in claim 1, wherein the first mode is a mode whose oscillations are essentially independent of the medium, and the second mode is a mode whose oscillations are essentially influenced by the medium.

8. The method as claimed in claim 7, wherein a change in the first mode whose oscillations are essentially independent of the medium is used to detect whether a change in mass has occurred at the oscillable unit (2).

9. The method as claimed in claim 7, wherein a change in frequency of the oscillations of the first mode is used to detect whether a change in mass has occurred at the oscillable unit (2).

10. The method as claimed in claim 7, further comprising the step of outputting an error message when changes in at least one of the first mode and the second mode of the oscillations of the oscillable unit, which changes are caused by the change in mass at the oscillable unit, overshoot a prescribed desired value.

11. The method as claimed in claim 7, further comprising the step of undertaking inline correction of the oscillation frequency of the oscillable unit based at least in part on a change, caused by a change in mass at the oscillable unit, in at least one of the first mode and the second mode of the oscillations of the oscillable unit.

12. The method as claimed in claim 1, wherein a change in the first mode whose oscillations are essentially independent of the medium is used to detect whether a change in mass has occurred at the oscillable unit (2).

13. The method as claimed in claim 12, wherein a change in frequency of the oscillations of the first mode is used to detect whether a change in mass has occurred at the oscillable unit (2).

14. The method as claimed in claim 12, further comprising the step of outputting an error message when changes in at least one of the first mode and the second mode of the oscillations of the oscillable unit, which changes are caused by the change in mass at the oscillable unit, overshoot a prescribed desired value.

15. The method as claimed in claim 12, further comprising the step of undertaking inline correction of the oscillation frequency of the oscillable unit based at least in part on a change, caused by a change in mass at the oscillable unit, in at least one of the first mode and the second mode of the oscillations of the oscillable unit.

16. The method as claimed in claim 1, wherein a change in frequency of the oscillations of the first mode is used to detect whether a change in mass has occurred at the oscillable unit (2).

17. The method as claimed in claim 16, further comprising the step of outputting an error message when changes in at least one of the first mode and the second mode of the oscillations of the oscillable unit, which changes are caused by the change in mass at the oscillable unit, overshoot a prescribed desired value.

18. The method as claimed in claim 16, further comprising the step of undertaking inline correction of the oscillation frequency of the oscillable unit based at least in part on a change, caused by a change in mass at the oscillable unit, in at least one of the first mode and the second mode of the oscillations of the oscillable unit.

19. The method as claimed in claim 1, wherein two modes are selected as first mode and as second mode of the oscillations of the oscillable unit (2), the two modes respectively having a first component which is a function of the medium, and the two modes having a second component which is essentially independent of the medium and depends essentially only on the respective mass of the oscillable unit (2).

20. The method as claimed in claim 19, further comprising the step of drawing conclusions on a mass of a coating which has formed on the oscillable unit, with the aid of a functional relationship of the first and second modes of the oscillations of the oscillable unit on the medium and on a mass of the oscillable unit.

21. The method as claimed in claim 20, further comprising the step of outputting an error message when changes in at least one of the first mode and the second mode of the oscillations of the oscillable unit, which changes are caused by the change in mass at the oscillable unit, overshoot a prescribed desired value.

22. The method as claimed in claim 20, further comprising the step of undertaking inline correction of the oscillation frequency of the oscillable unit based at least in part on a change, caused by a change in mass at the oscillable unit, in at least one of the first mode and the second mode of the oscillations of the oscillable unit.

23. The method as claimed in claim 19, further comprising the step of outputting an error message when changes in at least one of the first mode and the second mode of the oscillations of the oscillable unit, which changes are caused by the change in mass at the oscillable unit, overshoot a prescribed desired value.

24. The method as claimed in claim 19, further comprising the step of undertaking inline correction of the oscillation frequency of the oscillable unit based at least in part on a change, caused by a change in mass at the oscillable unit, in at least one of the first mode and the second mode of the oscillations of the oscillable unit.

25. The method as claimed in claim 1, further comprising the step of outputting an error message when changes in at least one of the first mode and the second mode of the oscillations of the oscillable unit, which changes are caused by the change in mass at the oscillable unit, overshoot a prescribed desired value.

26. The method as claimed in claim 1, further comprising the step of undertaking inline correction of the oscillation frequency of the oscillable unit based at least in part on a change, caused by a change in mass at the oscillable unit, in at least one of the first mode and the second mode of the oscillations of the oscillable unit.

27. An apparatus for determining at least one of a filling level and a density of a medium in a container, the apparatus comprising:
  an oscillable unit which is configured to be fitted to the container;
  a drive/reception unit which excites the oscillable unit to oscillate with the aid of a prescribed exciter frequency, and which receives oscillations of the oscillable unit; and
  a control/evaluation unit which detects that a predetermined filling level has been reached as soon as a prescribed change in frequency occurs, and which determines the density of the medium with the aid of an oscillation frequency of the oscillable unit;
  wherein the control/evaluation unit uses at least a first mode and a second mode of the oscillations of the oscillable unit which exist while the oscillable unit is in contact with the medium for the purpose of evaluation, and the control/evaluation unit detects a change in mass at the oscillable unit with the aid of the evaluated modes.

28. The apparatus as claimed in claim 27, wherein the evaluation/control unit is integrated into the apparatus for at least one of determining the filling level, monitoring the filling level , and determining the density of the medium.

29. The apparatus as claimed in claim 28, further comprising at least two data lines via which measured data are led to the evaluation/control unit.

30. The apparatus as claimed in claim 28, wherein an output unit (14) is provided which outputs an error message to the operating staff optically and/or acoustically when, preferably within the limits of prescribed tolerance values, a prescribed desired value of the change in frequency which is to be ascribed to a change in mass at the oscillable unit (2) is overshot or undershot.

31. The apparatus as claimed in claim 27, further comprising at least two data lines via which measured data are led to the evaluation/control unit.

32. The apparatus as claimed in claim 31, wherein the measured data and the data on the extent of the coating of the oscillable unit (2) are transmitted digitally to the remote control point (13).

33. The apparatus as claimed in claim 31, wherein an output unit (14) is provided which outputs an error message to the operating staff optically and/or acoustically when, preferably within the limits of prescribed tolerance values, a prescribed desired value of the change in frequency which is to be ascribed to a change in mass at the oscillable unit (2) is overshot or undershot.

34. The apparatus as claimed in claim 27, further comprising an output unit which outputs at least one of an optical error message and an acoustical error message to the operating staff when, preferably within the limits of prescribed tolerance values, a prescribed desired value of the change in frequency which is to be ascribed to a change in mass at the oscillable unit is at least one of overshot and undershot.

35. The apparatus as claimed in claim 34, wherein the control/evaluation unit (10) is assigned a storage unit (11) in which desired values are stored for tolerable changes in frequency which originate from a change in mass at the oscillable unit (2).

36. The apparatus as claimed in claim 27, wherein the control/evaluation unit (10) is assigned a storage unit (11) in which desired values are stored for tolerable changes in frequency which originate from a change in mass at the oscillable unit (2).

37. The apparatus as claimed in claim 10, further comprising at least two data lines via which the evaluation/control unit communicates with a remote control point.

38. The apparatus as claimed in claim 11, further comprising at least two data lines via which the evaluation/control unit communicates with a remote control point.

* * * * *